United States Patent [19]

Gittos et al.

[11] 3,935,207

[45] Jan. 27, 1976

[54] CONJUGATE ADDITION

[75] Inventors: Maurice W. Gittos, Slough; David Anthony Amey, Luton, both of England

[73] Assignee: Aspro-Nicholas Limited, Slough, England

[22] Filed: Dec. 18, 1973

[21] Appl. No.: 425,875

[30] Foreign Application Priority Data

Dec. 28, 1972 United Kingdom............ 59762/72

[52] U.S. Cl.. 260/247.5 R; 260/268 R; 260/293.69; 260/293.71; 260/293.75; 260/293.78; 260/295 R; 260/307 F; 260/326.2; 260/326.62; 260/326.8; 260/465 E; 260/468 J; 260/482 R; 424/248; 424/250; 424/267

[51] Int. Cl.$^2$........................................ C07D 295/00

[58] Field of Search .... 260/247.5 R, 465 E, 293.69, 260/293.71, 293.75, 326.2

[56] References Cited

OTHER PUBLICATIONS

Adams et al., Organic Reactions, Vol. 10, pp. 182–183, (1959).

Dimroth et al., Chem. Ber. 90, 2207 (1957).

*Primary Examiner*—Lorraine A. Weinberger
*Assistant Examiner*—P. J. Killos
*Attorney, Agent, or Firm*—Foster York

[57] ABSTRACT

Organic compounds are prepared by a novel method of conjugate addition in which a donor compound including a carbanion derived from an activated methylidyne group is treated with an acceptor compound including a carbon-carbon unsaturated bond conjugated with an onium ion derived from a polar functional group. The method has particular application as a step in the production of novel intermediates and novel pharmacologically active compounds as disclosed in the Applicants' co-pending application of even date.

11 Claims, No Drawings

CONJUGATE ADDITION

The present invention relates to the preparation of organic compounds by conjugate addition and provides a process for effecting such addition where a normal Michael reaction cannot be performed. In particular, but not exclusively, the invention provides a process for effecting conjugate addition where one of the carbon atoms of the acceptor across which the donor is to be added carries a substituent such as an alkyl or aryl group.

It is well known that a donor molecule including an activated methylidyne group (i.e. a carbon atom having at least one hydrogen atom attached thereto) will add across a pair of adjacent carbon atoms joined by an ethylenically or acetylenically unsaturated bond of an acceptor molecule in which said bond is conjugated with an electron attracting group. In a "normal" Michael reaction the addition takes place in the presence of alkaline reagents to yield a compound in which the donor carbanion derived from the donor molecule by removal of a proton from the methylidyne group is attached to the activated (i.e. less electron dense) carbon atom of the unsaturated moiety of the acceptor. Conjugate additions which result in the preparation of a compound in the aforementioned manner are referred to hereinafter as "normal" additions whether they are conventional Michael additions or other conjugated additions. However, in numerous cases the reaction between a molecule and an acceptor molecule under Michael reaction conditions fails to yield the "normal" product. For example, an "abnormal" Michael reaction may occur (see The Michael Reaction, Bergmann et al, organic Reactions, Vol 10, 1059, pp. 179–555.

The Inventors sought to prepare certain pharmacologically active 3-phenyl-3-aminoalkyl-2,6-dioxohydrogenated pyridines (see copending U.K. patent application No. 59761/72 and foreign counterparts thereof) from corresponding 2-phenyl-2-aminoalkylpentane or pent-3-ene-1,5-diacids or functional derivatives thereof such as nitrile esters by methods taught in U.S. Pat. Nos. 2,664,424 and 2,749,346. However, they found that, whereas the pentane or pentene reactants which were unsubstituted in the 3 and 4 positions could be prepared by normal Michael additions of the corresponding aminoalkyl benzyl cyanides across the unsaturated bond of acrylic or propiolic esters as taught in said Specifications, pentane or pentene reactants having a substituent, in particular an alkyl group, in the 3 and/or 4 positions could not be obtained by the corresponding Micheal additions. Thus, for example, the desired pentane and pentene reactants were obtained by a benzyl trimethyl ammonium hydroxide or alkoxide catalysed Michael addition of α(β-dimethylaminoethyl)benzyl cyanide to methyl acrylate and propiolate respectively but not when the acceptor molecule was methyl methacrylate, ethyl crotonate or ethyl tetrolate. In the case of the attempted "normal" additions using methyl methacrylate and ethyl crotonate a work-up designed to isolate basic organic materials yielded only the benzyl cyanide reactant. The attempted "normal" addition using ethyl tetrolate produced a basic product but which was not the desired pentene compound. Similar results were obtained when dimsyl sodium, i.e.

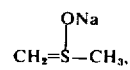

was used as catalyst instead of the weaker hydroxide or alkoxide base in said attempted "normal" Micheal additions. In all of the unsuccessful attempts, it is believed that an "abnormal" Michael reaction occurred.

The Inventors have found that a "normal" addition occurred when the aforementioned benzyl cyanide donor was used in the form of a salt of an carbanion derived from its methylidyne group, in particular an alkali metal salt, and the ester moiety of the acceptor was replaced by an onium salt, in particular the iminium salt of a corresponding amide. Thus, for example, when sodium α(β-dimethylaminoethyl)benzyl cyanide was treated with 1-(1-ethoxy-2-methylprop-2-enylidine)morpholinium tetrafluoroborate, normal conjugate addition occurred to yield 4-(β-dimethylaminoethyl)-4-cyano-4-phenyl)-2-methyl-1-ethoxy-1-morpholinobut-1-ene. The said product may readily be converted into a pentane reactant (e.g. 4-(β-dimethylamino-ethyl)-4-cyano-4-phenyl-2-methyl-butanoic acid ethyl ester) and thence to 3-phenyl-3-(β-dimethylamino-ethyl)-5-methyl-2,6-dioxo-piperidine. Alternatively, the said product may be cyclised directly to said piperidine compound.

The Inventors believe that their process is of general application to conjugate addition and provides a method of "normal" addition where such addition is not obtained using donors and acceptors in the nonionic form used in conventional Micheal additions.

According to the present invention, therefore, there is provided a method of conjugate addition which comprises treating a donor compound including a carbanion derived from an activated methylidyne group with an acceptor compound including a carbon- carbon ethylenically or acetylenically unsaturated bond conjugated with an onium ion derived from a polar functional group. The invention may be alternatively defined as a modified Michael addition in which the donor compound is in the form of a cation salt of the carbanion of its methylidyne group and the acceptor compound is in the form of an anion salt of an onium ion derived from its conjugated polar functional group.

In the special case where the acceptor has a methylidyne group on the α carbon atom, the said cation and anion can be the onium ion of the acceptor and the carbanion of the donor respectively. The donor and the acceptor reactants used in the process of the present invention may be obtained from any of those classes of methylidyne and unsaturated compounds respectively known or expected to react together in normal or abnormal Michael additions.

The methylidyne group of the donor molecule usually will be activated, i.e. made less electron dense, by the presence in the molecule of a polar functional group (i.e. electron withdrawing group), for example, nitrile, alkoxycarbonyl or nitro. Such activation is well known in the art in connection with conventional Michael reactions.

The donor molecule is in the form of a salt with a sufficiently strong base to convert the methylidyne group into a carbanion. Suitable bases will vary according to the acidity of the donor but alkali metal salts are expected to be of general use. Other salts which may be used in certain cases are alkaline earth metal, ammonium, quaternary ammonium, immonium and tertiary amine salts.

Having regard to the inventors' original desire to prepare certain 2-phenyl-2-aminoalkyl pentane and pentene derivatives, a presently preferred class of donor compound are alkali metal-α-aminoalkyl benzyl cyanides, especially those of the formula 1:

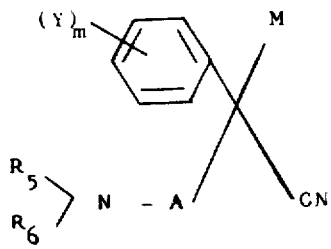

1.

wherein Y represents $C_1$-$C_4$ alkyl optionally substituted by hydroxy or by $C_1$-$C_4$ alkoxy, hydroxy, $C_1$-$C_4$ alkoxy, halogen or trifluoromethyl;

m represents zero or an integer up to 5;

A represents $C_1$-$C_6$ alkylene;

$R_5$ represents $C_1$-$C_4$ alkyl optionally substituted by $C_3$-$C_6$ cycloalkyl or $C_3$ to $C_6$ cycloalkyl, and $R_6$ represents hydrogen or $C_1$-$C_4$ alkyl optionally substituted by phenyl (including substituted phenyl, especially dialkoxy phenyl) or $R_5$ together with $R_6$ represents an alkylene radical optionally interrupted by oxygen or nitrogen and which together with the amino nitrogen atom constitutes a saturated five or six-membered heterocyclic ring; and M represents a cation, especially an alkali metal, particularly sodium.

Specially preferred donor compounds are those of the formula 1 above in which

Y represents $C_1$-$C_4$ alkoxy, especially methoxy, halogen, especially chlorine, or trifluoromethyl;

m represents zero or 1;

A represents $C_1$-$C_6$ alkylene especially of the formula —$(CH_2)_n$— where n represents 2, 3 or 4;

$R_5$ represents $C_1$-$C_4$ alkyl, especially methyl or ethyl;

$R_6$ represents hydrogen or, preferably $C_1$-$C_4$ alkyl especially methyl or ethyl; and M represents an alkali metal.

Particularly preferred donor compounds are those of the formula 1 in which

Y represents methoxy;

m represents 1;

A represents ethylene or n-propylene;

$R_5$ and $R_6$ independently represent methyl or ethyl and

M represents sodium.

The said preferred donors may be prepared in situ by treating the corresponding benzyl cyanide with a molar equivalent amount of a very strong alkali metal base such as dimsyl sodium (obtained by dissolving sodium hydride in dimethylsulphoxide) in a polar aprotic solvent. The temperature of this reaction may be up to about 50°C but should be below the boiling point of the solvent.

The onium ion of the acceptor molecule is derived from an electron withdrawing group (i.e. polar functional group) which is conjugated with the unsaturated bond of the molecule. Said group may be any of those used in conventional Michael additions and which readily form an onium ion, for example cyano, tertiary amide, alkoxy-thiocarbonyl, alkylthio-carbonyl, carbonyl, thiocarbonyl and substituted imine. Usually, the onium ions will be prepared by alkylation of the said electron withdrawing groups as follows:

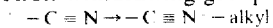

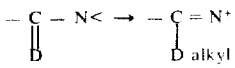

(where D represents a Group VIa element of Mendeleef's Periodic Classification, especially oxygen or sulphur).

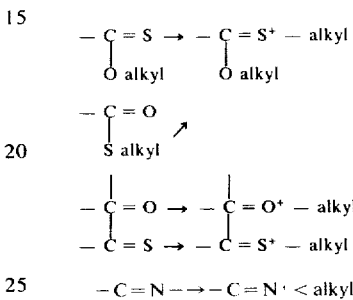

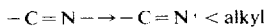

$-C=N-\rightarrow-C=N^+<$ alkyl

The said alkylation can be performed by treating the corresponding acceptor compound including the non-ionised electron withdrawing group from which the onium ion is to be derived with a compound including an incipient alkyl carbonium ion. Usually the reaction will be carried out in a polar solvent such as dichlormethane at a temperature in the range 20° to 80°C, preferably under reflux.

Alkyl carbonium ions are positively charged intermediates formed by the removal of a pair of electrons from a carbon atom of a monovalent hydrocarbon radical. They have only a transient existence as such but do exist in solvated form such as in trialkyloxonium (e.g. alkyl$_3$o$^+$) and dialkyloxycarbonium (e.g. HC$^+$(Oalkyl)$_2$) ions. Conveniently such solvated ions are supplied to the reaction mixture in combination with such non-nucleophilic anions such as

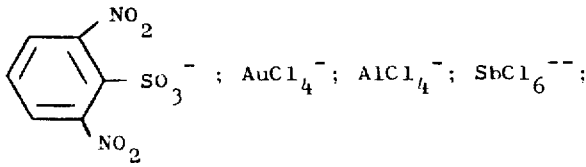

PtO$_6$$^{--}$ and, preferably BF$_4$$^-$. Another suitable source of incipient alkyl carbonium ions are the alkyl esters of very strong acids such as fluorosulphonic acid (FSO$_3$H) and perfluorinated alkyl sulphonic acids such as CF$_3$SO$_3$H and C$_4$F$_9$SO$_3$H. In the present case a preferred class of compounds containing an incipient carbonium ion are the trialkyloxonium tetrafluoroborates. Another preferred class are the methyl and ethyl esters of fluorosulphonic acid. In a typical process a solution of triethyloxonium tetrafluoroborate (1 equivalent) in dichloromethane is added to an acryloyl or propioloyl amide (1 equivalent) in the same solvent. The mixture is refluxed for 30 minutes and then the solvent removed under reduced pressure. The product is dissolved in dimethylsulphoxide for immediate use or is triturated with ethylacetate and the solid filtered off and dried.

The anion associated with the onium ion usually will be a non-nucleophilic anion, for example that present in the alkylating agent selected to react with the non-ionic acceptor compound. Thus, suitable anions are those of the aforementioned compounds including an incipient carbonium ion and especially $BF_4^-$ and $FSO_3^-$.

The invention has particular application to those acceptor compounds which have a substituent on one or more of the carbon atoms joined by the conjugated unsaturated bond. Such acceptor compounds appear to be particularly susceptible to "abnormal" Michael reactions. Examples of said substituents are alkyl, such as methyl and ethyl; aralkyl, such as benzyl; hydroxyalkyl; alkoxyalkyl; alkoxycarbonyl; and aryl such as phenyl, thienyl, furyl, pyrrolyl and tetrazolyl.

Having regard to the Inventor's original desire to prepare certain pentane or pentene-1,5-diacids and derivatives thereof, in particular the nitrile alkylesters, a presently preferred class of acceptor compound are those of the formula 2:

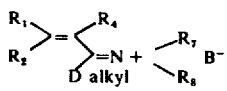

2.

wherein
- $R_1$ and $R_2$ independently represent hydrogen or $C_1$-$C_4$ alkyl and $R_4$ represents hydrogen, $C_1$-$C_4$ alkyl or $C_2$-$C_5$ alkoxycarbonyl provided that at least one of $R_1$, $R_2$ and $R_4$ represents alkyl or
- $R_1$ together with $R_2$ or $R_4$ represents an alkylene radical which together with their adjacent carbon atom(s) forms a carbocyclic ring of 3 to 8 carbon atoms and $R_4$ or $R_2$ respectively is as defined above, or
- $R_1$ together with $R_4$ represents a third valency bond joining their adjacent ring carbon atoms and $R_2$ represents $C_1$-$C_4$ alkyl;
- $R_7$ and $R_8$ represent the same or different alkyl radicals or together represent a saturated alkylene radical optionally substituted by oxygen or nitrogen which with the adjacent nitrogen atom forms a heterocyclic ring, especially piperidine, pyrrolidine, piperazine and, preferably, morpholine;
- D represents a Group VIa element especially sulphur and preferably oxygen; and
- $B^-$ represents a non-nucleophilic anion, especially tetrafluoroborate or fluorosulphonate.

Specially preferred compounds of the formula 2 are those in which
- $R_1$, $R_2$ and $R_4$ independently represent hydrogen or $C_1$-$C_4$ alkyl, especially methyl, provided that at least one of $R_1$, $R_2$ and $R_4$ represents alkyl or
- $R_1$ together with $R_4$ represents a third valency bond joining their adjacent carbon atoms and $R_2$ represents $C_1$ to $C_4$ alkyl;
- $R_7$ and $R_8$ represent the same or different $C_1$-$C_4$ alkyl, especially methyl or ethyl, or together represent a saturated alkylene radical which with the adjacent nitrogen atom forms a piperidine, pyrrolidine, piperazine or morpholine ring,
- D represents sulphur or, especially oxygen, and
- $B^-$ represents a non-nucleophilic anion, especially tetrafluoroborate or fluorosulphonate.

The iminium salts of formula 2 are believed to be new compounds and as such are comprised in the present invention. They can be prepared by treating the corresponding alkyl or alkylene substituted acryloyl or propioloyl amide or its Group VIa element analogue with an alkylating agent, preferably with a compound including an incipient carbonium ion as described above.

The substituted acryloylamides and their Group VIa analogues can be prepared by treatment in an inert organic solvent of the corresponding acryloyl anhydride, chloride or bromide or analogue thereof with the corresponding dialkylamine or saturated heterocyclic amine at a temperature in the range $-10°$ to $+15°C$. In a typical process, an acryloyl chloride (1 equivalent) is dissolved in dry ether or benzene and then ice-cooled. The amine (2 equivalents) is added to the solution whilst stirring well and when the addition is complete the mixture is warmed for a few minutes, cooled and amine hydrochloride filtered off and the solvent removed. The amide product thus obtained is recrystallised from petrol or dissolved in dichloromethane for immediate use.

The substituted propioloyl amides and their Group VIa analogues can be prepared from alkali metal salts of the corresponding terminal acetylene by reaction with a carbamoyl chloride or bromide. Usually, the reaction will be carried out at a temperature in the range $-20°$ to $+40°C$ in a polar aprotic solvent under an inert gas atmosphere. The alkali metal salt reactant can be obtained by treating a terminal acetylene with a strong alkali metal base in an aprotic solvent at a temperature in the range $-50°$ to $-20°C$ under an inert gas atmosphere. In a typical process, a terminal acetylene in approximately 50% excess is bubbled through a solution of butyl lithium in hexane at $-40°C$ and under a nitrogen atmosphere. The mixture is stirred and allowed to warm up to about $-20°C$, whence dry tetrahydrofuran is added to dissolve the lithium salt of the acetylene and then a solution of carbamoyl chloride also in dry tetrahydrofuran is added. The mixture is allowed to increase to room temperature and is then heated to 50°C for 15 minutes. Lithium chloride is filtered off and the propioloyl amide isolated by removal of the solvent. In exceptional cases, it may be necessary to dissolve the lithium chloride in a minimum of water and then extract the amide into chloroform.

When a donor compound of formula 1 reacts with an acceptor compound of formula 2, the product will be a but-1-ene or but-1,2-diene of formula 3:

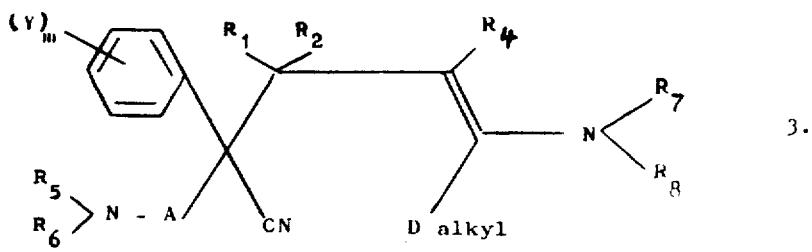

3.

wherein the symbols are as defined in connection with formulae 1 and 2. These compounds may readily be converted into pharmacologically active 2,6-dioxohydrogenated pyridines by methods disclosed in our copending U.K. patent application No. 59761/72, the disclosure of which application is incorporated herein by reference, pertinent portions of which are as follows:

The present invention relates to compounds having pharmacological, in particular central nervous system, especially anti-depressant, activity and provides pharmacologically active 3-phenyl-3-aminoalkyl-2,6-dioxohydrogenated pyridines and methods for their preparation. The invention provides also pharmaceutical compositions containing one or more of said pyridine derivatives and methods of treatment which comprise administering to an animal a pharmacologically effective dose of one or more of said derivatives.

It is known that 3-phenyl-3-aminoalkyl-2,6-dioxotetra- and hexa-hydropyridines optionally substituted in the 1-position by an alkyl group but otherwise unsubstituted in the hydrogenated pyridine ring have pronounced parasympatholytic activity (see U.S. Pat. Nos. 2,644,424 and 2,749,346). A well known example of such parasympatholytic compounds is Aturbane, i.e. 3-phenyl-3-(β-diethylaminoethyl)-2,6-dioxo-piperidine (see The Extra Pharmacopoeia, Martindale, 26th Edition at page 304).

The inventors have now unexpectedly found that the parasympatholytic activity of 3-phenyl-3-aminoalkyl-2,6-dioxo-tetra- and hexa-hydropyridines can be significantly reduced and a useful central nervous system, especially antidepressant, activity developed by introducing into the hydrogenated pyridine ring certain substituents in the 4 and/or 5 positions.

According to the present invention, therefore, there are provided 3-phenyl-3-aminoalkyl-2,6-dioxo-tetra and hexahydropyridines which are substituted in at least one of the 4 and 5 positions of the hydrogenated pyridine ring by a $C_1$–$C_4$ alkyl radical or an alkylene radical which together with at least one of the carbon atoms at said 4 and 5 positions forms a carbocyclic ring of 3 to 8 carbon atoms, and acid addition salts and quaternary ammonium derivatives thereof.

A preferred class of compounds of the present invention are those of formula 1;

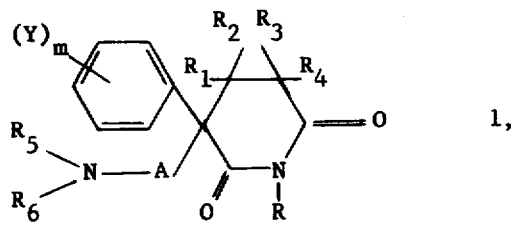

1, wherein
R represents hydrogen or $C_1$–$C_4$ alkyl;

$R_1$, $R_2$ and $R_3$ independently represent hydrogen or $C_1$–$C_4$ alkyl and $R_4$ represents hydrogen, $C_1$–$C_4$ alkyl or $C_2$–$C_5$ alkoxycarbonyl, provided that at least one of $R_1$, $R_2$, $R_3$ and $R_4$ represents alkyl, or $R_1$ together with $R_2$ or with $R_3$ represents an alkylene radical which together with their adjacent carbon atom(s) of the hydrogenated pyridine ring forms a carbocyclic ring of 3 to 8 carbon atoms and $R_3$ or $R_2$ respectively and $R_4$ are as defined above (not subject to the proviso), or $R_2$ and $R_4$ together represent a second valency bond joining their adjacent carbon atoms, or $R_1$ together with $R_3$ represents a second valency bond joining their adjacent ring carbon atoms and $R_2$ and $R_4$ are as defined above provided that at least one of them represents alkyl;

Y represents $C_1$–$C_4$ alkyl optionally substituted by hydroxy or $C_1$–$C_4$ alkoxy, hydroxy, $C_1$–$C_4$ alkoxy, halogen or trifluoromethyl;

m represents zero or an integer up to 5;

A represents $C_1$–$C_6$ alkylene; and $R_5$ represents $C_1$–$C_4$ alkyl optionally substituted by $C_3$–$C_6$ cycloalkyl, or $C_3$–$C_6$ cycloalkyl and $R_6$ represents hydrogen or $C_1$–$C_4$ alkyl optionally substituted by phenyl, or $R_5$ together with $R_6$ represents an alkylene radical optionally interrupted by oxygen or nitrogen and which together with the amino nitrogen atom constitutes a saturated six-membered heterocyclic ring, and acid addition salts and quaternary ammonium derivatives thereof.

U.S. Pat. No. 2,664,424 teaches that 3-phenyl-3-aminoalkyl-2,6-dioxo-piperidines can be prepared (1) by reacting the corresponding 2-phenyl-2-aminoalkyl-pentane-1,5-diacids or functional derivatives thereof, such as their anhydrides or halides, with ammonia or amines, or (2) by heating the diamides or diammonium salts of said pentane diacids, or (3) by intramolecular acylation of the corresponding pentane-1,5-diacid monoamides or their functional derivatives. In the latter reaction, the monoamide or its functional derivative is not usually used as a reactant but is formed during the course of the treatment of the corresponding pentane-1,5-diacid-dinitriles, nitrile esters or, more usually, mononitriles with condensing agents to yield the desired dioxopiperidines. Analogous methods of preparing 3-phenyl-3-aminoalkyl-2,6-dioxotetrahydropyridines from 2-phenyl-2-aminoalkyl-pent-3-ene-1,5-diacids and derivatives thereof are described in U.S. Pat. No. 2,749,346.

All of the aforementioned prior art processes can be used to prepare compound of the present invention from the corresponding 2-phenyl-2-aminoalkyl-3 and-/or 4-substituted-pentane or pent-3-ene-1,5-diacids and derivatives thereof.

In terms of preparing compounds of formula 1, the said butene or butadiene starting material will be of the formula 3:

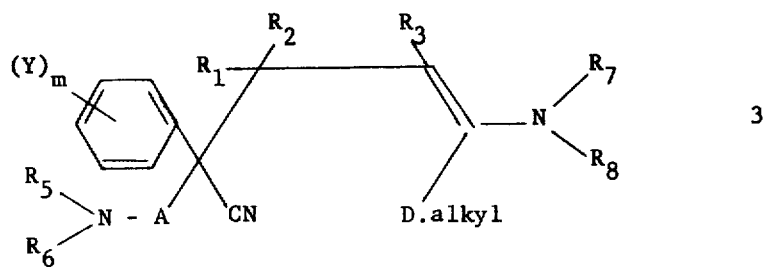

3 wherein D represents a Group VIa element, especially oxygen or sulphur;

R₇ and R₈ represent the same or different alkyl groups or together represent a saturated alkylene radical optionally substituted by oxygen or nitrogen which with the adjacent nitrogen atom forms a heterocyclic ring, and the remaining symbols are as defined in connection with formula 1.

The process for converting the butene or butadiene starting materials into the desired nitrile ester comprises a first step in which the corresponding 4-aminoalkyl-4-cyano-4-phenyl-3 and/or 2 alkyl or alkylene-1-dialkoxy-1-alkoxy or Group VIa element analogue-butane or but-2-ene is formed by treating the starting material with, for example, a strong non-nucleophilic acid, such as methane sulphonic acid, in the presence of a mixture of a $C_1$–$C_6$ primary alcohol, such as ethanol, and an orthoester, such as ethyl orthoformate. The reaction usually will be carried out at an elevated temperature, advantageously in the range 60° to 120°C and preferably under reflux conditions. When the intermediate compound is required for the preparation of a compound of formula 1, it will have the formula 4:

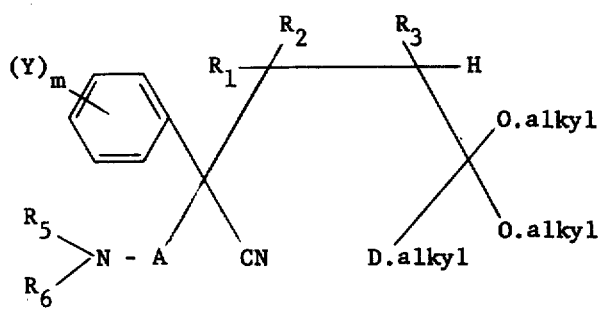

4 wherein the symbols are as defined in connection with formulae 1 and 3.

The butane or butene intermediate prepared as above is then hydrolysed, usually in situ, by treatment with, for example, water at an elevated temperature, especially 60° to 90°C, to the desired nitrile ester. This ester may then be treated with a condensing agent to form a compound of the invention in the manner described above. However, since the ester is liable to a competitive reaction with the original amine starting material, it is preferred to subject the reaction product of the hydrolysis step to a Schotten-Baumann reaction with, for example, p-toluene sulphonyl chloride.

In a typical process for preparing compounds of the invention from the aforementioned butene and butadiene starting materials, the starting material (1 equivalent) is dissolved in ethanol and ethyl orthoformate (5 equivalents) and methane sulphonic acid (3 equivalents) added to the resultant solution. Said solution is refluxed overnight and then poured into water. The aqueous mixture is maintained at 70°C for 30 minutes and then cooled, washed with ether, adjusted to pH7 and added to a suspension of p-tolulene sulphonyl chloride in 5N sodium hydroxide. The mixture is shaken vigorously for 15 minutes with cooling, if necessary.

The product is extracted into ether, the ethereal solution washed with dilute hydrochloric acid and the aqueous solution added to saturated potassium carbonate solution. The basic organic materials are then extracted into ether and recovered by drying over mangesium sulphate and evaporating off the solvent. The nitrile ester product thus obtained will be contaminated with some corresponding amide which may be separated by column chromatography. This nitrile ester, after separation or still in admixture with the contaminant amide, is dissolved in acetic acid (1 ml per gm of ester) and sulphuric acid (equal volume with acetic acid) and the resultant solution held at 100°C for at least 1 hour before pouring onto an ice and ammonium hydroxide mixture. The amount of ammonium hydroxide in the mixture should be in excess of that required to exactly neutralise the acid and sufficient to bring the pH of the final solution into the range 7.5 to 9.5. The desired compound of the invention is then extracted into a suitable solvent such as chloroform and subsequently recrystallised from a suitable solvent, e.g. ethanol.

In the composition aspect of the invention, there are provided pharmaceutical formulations in which form the active compounds of the invention will normally be utilised. Such formulations are prepared in a manner known per se in the pharmaceutical art and usually comprise at least one active compound of the invention in admixture or otherwise in association with a pharmaceutically acceptable carrier therefor.

The formulations of the invention may be adapted for enteral or parenteral use and may be administered to a subject requiring treatment in the form of tablets, capsules, suppositories, solutions, suspensions or the like. The dosage required for the treatment of any animal will depend upon the route of administration and will usually fall within the range 0.01 to 250 mg/kg daily. In the case of humans much further work remains to be done before a safe and effective dosage can be recommended but it is expected that said dosage will be within the range 0.1 to 100 mg/kg daily. Accordingly, formulations of the invention are likely to be provided in dosage unit forms containing from 1 to 1000 mg, more likely 5 to 500 mg and most likely 10 to 250 mg.

The following Examples will further illustrate the preparation of the novel compounds of this invention. All temperatures are given in degrees Centigrade.

EXAMPLE 1

Preparation of
3-(m-methoxyphenyl)-3-(γ-N.N-dimethylamino-
propyl)-4,4-dimethyl-2,6-dioxo-piperidine.

Sodium hydride (3.36 g of a 50% suspension in oil, 0.07 mole) is placed in a 3-necked round-bottomed flask and the mineral oil removed by washing (twice) with 40–60 petrol. The flask is then fitted with a stirrer, condenser and nitrogen bleed and dry dimethylsulphoxide (75 ml) added. The mixture is stirred in a nitrogen atmosphere at temperatures of up to 80° until the sodium hydride has completely dissolved and evolution of phdrogen has ceased. The resultant solution of dimsyl sodium is then cooled and α(3-N,N-dimethylaminopropyl)-m-methoxy benzyl cyanide (16.2 gm, 0.07 mole) added followed by dropwise addition of a solution in dry dimethylsulphoxide of 3,3-dimethyl-1-ethoxy-prop-2-enylidine morpholinium tetrafluoroborate (20 gm, 0.07 mole). When addition is complete, the mixture is held at 50° for 30 minutes, cooled, transferred to a single-necked round-bottomed flask and the solvent removed under reduced pressure (1 mm Hg). The residue is triturated with dry ether and sodium tetrafluoroborate filtered off. The solid is further washed with dry ether and the washings added to the filtrate. The ether is then evaporated off to leave 4-(m-methoxyphenyl)-4-(γ-N,N-dimethylaminopropyl)-4-cyano-3,3-dimethyl-1-ethoxy-1-morpholino-but-1-ene (28.5 gm, 95%).

The but-1-ene product above is dissolved in acetic acid (45 ml) and sulphuric acid (30 ml) added. The resultant mixture is maintained at 100° until cyclisation is complete, as determined by working-up an aliquot and studying the infrared spectrum of the product. The solution is cooled and poured into excess ammonia/ice, the pH adjusted to about 8 with aqueous ammonia and the solution extracted with chloroform (three times). The organic solutions are combined, dried, filtered and the solvent removed. The residual dione is crystallised and recrystallised from ethanol to give white crystals of 3-(m-methoxyphenyl)-3-(γ-N,N-dimethylaminopropyl)-4,4-dimethyl-2,6-dioxo-piperidine, m.pt. 167°–9°.

The alkyl or alkylene radicals (including moieties) referred to in this Specification may be straight or branched chain, saturated or unsaturated hydrocarbon radicals. Unless otherwise stated, it is preferred that each hydrocarbon radical is saturated and contains 6, more especially 4, carbon atoms or less. Any reference in this Specification to a specific alkyl or alkylene radical having structural isomers includes all of those isomers and mixtures thereof unless a particular isomer is specified. Examples of alkyl radicals are methyl, ethyl, propyl, butyl, amyl, hexyl, ethenyl, ethynyl, propenyl (especially allyl), propynyl (especially propargyl), butenyl and butynyl. In the compounds of formulae 1,2 and 3 herein preferred alkyl radicals are methyl and ethyl and preferred alkylene radicals are 1,2-ethylene and 1,3-propylene for the alkylene moiety of the aminoalkyl group and 1,4-butylene and 1,5-hexylene for $R_1$ and $R_2$ or $R_3$.

The conjugate addition of the present invention can be carried out in an inert organic solvent, preferably a polar aprotic solvent such as dimethylsulphoxide or 1,4-dioxan. Generally, the reaction conditions are those conventionally used for Michael condensations other than the presence of an alkaline catalyst which is superfluous having regard to the salt form of the donor compound. Usually a solution of one of the reactants will be added dropwise to a solution of the other reactant whilst, if necessary, cooling the reaction mixture to dissipate the heat of reaction and then the reaction mixture heated to a temperature of up to about 75°C for a period of up to about 3 hours.

In a typical process, an iminium salt of the acceptor compound in dimethylsulphoxide is added dropwise with stirring to an equivalent amount of the donor salt in the same solvent. When the addition is complete, the mixture is maintained at 60°C for 2 hours, allowed to cool and transferred to a suitable vessel where the solvent is removed under pressure. The residue is triturated with ether and the mixture filtered. The filtrate is then evaporated down to a residue of the desired butene or butadiene.

As stated previously, it is believed that the process of the present invention is of general application to donors and acceptors of the specified type but, as with most if not all chemical reactions of general application, there will be reactants which will not undergo the desired addition. In particular, if a reactant has a site, for example a substituent group, which is more active with respect to the other reactant under the reaction conditions than the site required for the desired reaction, reaction will occur at said more active site in preference to, and possibly to the exclusion of, the addition reaction. Further, the presence of substituent groups may sterically hinder the desired reaction. These and other factors may prevent the use of certain reactants and/or combinations of reactants in the process of the present invention and as far as possible account should be taken of this when selecting the reactants. However, the presence of both reactants in salt form is believed to prevent an "abnormal" addition from occurring in preference to the "normal" addition.

In addition to the preparation of novel intermediates of formula 3, the process of the present invention can be used to prepare numerous known compounds having various uses, but principally as intermediates in the synthesis of directly useful chemical compounds.

The following Examples will further illustrate the novel preparation and novel intermediate iminium salts of this invention. All temperatures are given in degrees Centigrade.

EXAMPLE 1

Preparation of
4-(m-methoxyphenyl)-4-(γ-N,N-dimethylaminopropyl)-4-cyano-3,3-dimethyl-1-ethoxy-1-morpholino-but-1-ene Sodium hydride (3.36 g of a 50% suspension in oil, 0.07 mole) is placed in a 3-necked round bottomed flask and the mineral oil removed by washing (twice) with 40–60 petrol. The flask is then fitted with a stirrer, condenser and nitrogen bleed and dry dimethylsulphoxide (75 ml) added. The mixture is stirred in a nitrogen atmosphere at temperatures of up to 80° until the sodium hydride has completely dissolved and evolution of hydrogen has ceased. The resultant solution of dimsyl sodium is then cooled and α(3-N,N-dimethylaminopropyl)-m-methoxy benzyl cyanide (16.2 gm, 0.07 mole) added followed by dropwise addition of a solution in dry dimethylsulphoxide of 3,3-dimethyl-1-ethoxy-prop-2-enylidine morpholinium tetrafluoroborate (20 gm, 0.07 mole). When addition is complete, the mixture is held at 50° for 30 minutes, cooled, transferred to a single-necked round-bottomed flask and the solvent removed under reduced pressure (1mm Hg). The residue is triturated with dry ether and sodium tetrafluoroborate filtered off. The solid is further washed with dry ether and the washings added to the filtrate. The ether is then evaporated off to leave 4-(m-methoxyphenyl)-4-(γ-N,N-dimethylaminopropyl)-4-cyano-3,3-dimethyl-1-ethoxy-1-morpholino-but-1-ene (28.5 gm, 95%).

The 3,3-dimethyl-1-ethoxy-prop-2-enylidene morpholinium tetrafluoroborate reactant was obtained as follows:

Morpholine (2 equivalents) is added to a well-stirred ice-cooled solution in dry ether of 3,3-dimethylacryloyl chloride (1 equivalent) and when addition is complete, the mixture is warmed for a few minutes. the mixture is then cooled, filtered, the solvent removed and the residue recrystallized from 60-80 petrol to give 3,3-dimethylacryloyl morpholine m.pt. 52°-4°.

The 3,3-dimethylacryloyl morpholine (1 equivalent) obtained as above was dissolved in dichloromethane and triethyl oxonium-tetrafluoroborate (1 equivalent) in dichloromethane added to the resultant solution. The mixture was refluxed for 30 minutes, the solvent removed under reduced pressure, and the residue triturated with ethyl acetate and the solid filtered off and dried to yield the desired iminium tetrafluoroborate.

EXAMPLE 2

The following compounds of the invention have also been prepared by methods similar to those of Example 1:

a. 4-cyano-4-(β-dimethylaminoethyl)-1-ethoxy-2-methyl-1-morpholino-4-phenyl but-1-ene;
b. 4-cyano-4-(β-dimethylaminoethyl)-1ethoxy-3-methyl-1-morpholino-4-phenyl but-1-ene;
c. 4-cyano2,3-dimethyl-4-(βdimethylaminoethyl)-1-ethoxy-1-morpholino-4-phenyl but-1-ene;
d. 4-cyano-3,3-dimethyl-4-(β-dimethylaminoethyl)-1-ethoxy-1-morpholino-4-phenyl but-1-ene;
e. 4-cyano-4-(β-dimethylaminoethyl)-1-ethoxy-2-methyl-4-(3'-methoxyphenyl)-1-morpholino but-1-ene;
f. 4-cyano-4-(β-dimethylaminoethyl)-1-ethoxy-3-methyl-4-(3'-methoxyphenyl)-1-morpholino but-1-ene;
g. 4-cyano-3,3-dimethyl-4-(β-dimethylaminoethyl)-1-ethoxy-4-(3'-methoxyphenyl)-1-morpholino but-1-ene;
h. 4-cyano-3,3-dimethyl-4-(γ-dimethylaminopropyl)-1-ethoxy-4-phenyl-1-morpholino but-1-ene;
i. 4-cyano-4-(4'-chlorophenyl)-3,3-dimethyl-4-(γ-dimethylaminopropyl)-1-ethoxy-1-morpholino but-1-ene;
j. 4-cyano-2,3-dimethyl-4-(β-dimethylaminoethyl)-1-ethoxy-4-(3'-methoxyphenyl)-1-morpholino but-1-ene;
k. 4-cyano-4-(β(N-benzyl-N-methylamino)ethyl)-3,3-dimethyl-1-ethoxy-1-(4-morpholino)-4-phenyl but-1-ene;
l. 4-cyano-4-(β-dimethylaminoethyl)-1-dimethylamino-1-ethoxy-3-methyl-4-phenyl but-1,2-diene; and
m. 4-cyano-4-(βdimethylaminoethyl)-1-ethoxy-3-methyl-4-phenyl-1-pyrrolidino but-1-ene.

We claim:
1. A method of conjugate covalent addition which comprises treating a donor compound with an acceptor compound, said donor having the formula

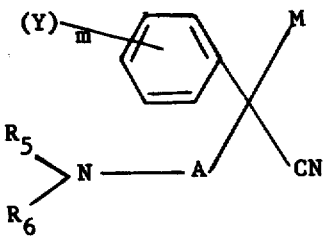

wherein y represents $C_1$–$C_4$ alkyl optionally substituted by hydroxy or by $C_1$–$C_4$ alkoxy, hydroxy, $C_1$–$C_4$ alkoxy, halogen or trifluoromethyl;
m represents zero or an integer up to 5;
A represents $C_1$–$C_6$ alkylene;
$R_5$ represents $C_1$–$C_4$ alkyl optionally substituted by $C_3$–$C_6$ cycloalkyl or $C_3$–$C_6$ cycloalkyl; and
$R_6$ represents hydrogen or $C_1$–$C_4$ alkyl optionally substituted by phenyl; or
$R_5$ and $R_6$ together represent an alkylene radical optionally interrupted by oxygen or nitrogen and which together with the amino nitrogen atom constitutes a saturated five or six-membered heterocyclic ring; and
M represents a cation;
and said acceptor having the formula

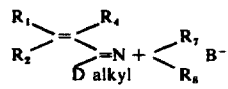

wherein $R_1$ and $R_2$ independently represent hydrogen or $C_1$–$C_4$ alkyl and $R_4$ represents hydrogen, $C_1$–$C_4$ alkyl or $C_2$–$C_5$ alkoxycarbonyl provided that at least one of $R_1$, $R_2$ and $R_4$ represents alkyl or
$R_1$ together with $R_2$ or $R_4$ represents an alkylene radical which together with their adjacent carbon atom(s) forms a carbocyclic ring of 3 to 8 carbon atoms and $R_4$ or $R_2$ respectively is as defined above, or
$R_1$ together with $R_4$ represents a third valency bond joining their immediately adjacent carbon atoms and $R_2$ represents $C_1$–$C_4$ alkyl;
$R_7$ and $R_8$ represent the same or different alkyl radicals or together represent a saturated alkylene radical optionally substituted by oxygen or nitrogen which with the adjacent nitrogen atom forms a heterocyclic ring;
D represents Q or S and
B⁻ represents a non-nucleophilic anion.

2. A method as claimed in claim 1 wherein the acceptor compound has a methylidyne group on the α carbon atoms and the cation of said carbanion and the anion of said onium ion are constituted by said onium ion and cation respectively.

3. A method as claimed in claim 1 wherein the donor is an alkali metal, alkaline earth metal, ammonium, immonium, quaternary ammonium or tertiary amine salt.

4. A method as claimed in claim 1 wherein the cation M is an alkali metal.

5. A method as claimed in claim 1 wherein B⁻ represents tetrafluoroborate or fluorosulphonate.

6. A method as claimed in claim 1 wherein the heterocyclic ring of the acceptor compound is piperidine, pyrrolidine, piperazine or morpholine.

7. A method as claimed in claim 1 wherein the conjugate addition reaction is carried out in an inert organic solvent.

8. A method as claimed in claim 16 wherein the inert organic solvent is a polar aprotic solvent.

9. A method as claimed in claim 1 wherein $R_7$ and $R_8$ together represent a saturated alkylene radical substituted by oxygen which with the adjacent nitrogen atom forms a morpholine ring.

10. The method of claim 1 wherein D is O.

11. The method of claim 1 wherein D is S.

* * * * *